United States Patent
McInroy (10) Patent No.: US 10,076,586 B2
(45) Date of Patent: Sep. 18, 2018

(54) WOUND DRESSINGS

(71) Applicant: KCI USA, Inc., San Antonio, TX (US)

(72) Inventor: Lorna McInroy, Earby (GB)

(73) Assignee: KCI USA, INC., San Antonio, TX (US)

(*) Notice: Subject to any disclaimer, the term of this patent is extended or adjusted under 35 U.S.C. 154(b) by 138 days.

(21) Appl. No.: 14/398,696

(22) PCT Filed: May 1, 2013

(86) PCT No.: PCT/IB2013/053448
§ 371 (c)(1),
(2) Date: Nov. 3, 2014

(87) PCT Pub. No.: WO2013/164774
PCT Pub. Date: Nov. 7, 2013

(65) Prior Publication Data
US 2015/0096912 A1    Apr. 9, 2015

(30) Foreign Application Priority Data

May 2, 2012    (GB) .................................. 1207617.0

(51) Int. Cl.
*A61F 13/00*    (2006.01)
*A61L 15/24*    (2006.01)
(Continued)

(52) U.S. Cl.
CPC ............ *A61L 15/24* (2013.01); *A61F 15/002* (2013.01); *A61L 15/325* (2013.01); *A61L 15/44* (2013.01);
(Continued)

(58) Field of Classification Search
CPC .... A61K 2300/00; A61K 38/39; A61K 33/38; A61K 6/0017; A61K 6/0023;
(Continued)

(56) References Cited

U.S. PATENT DOCUMENTS 4,552,138 A * 11/1985 Hofeditz ............. A61L 26/0014
424/445
5,128,136 A * 7/1992 Bentley .................. A01N 59/12
424/443
(Continued)

FOREIGN PATENT DOCUMENTS

EP         1795210 A2    6/2007
WO    WO 2010062587 A1 *  6/2010    ............... C07K 7/08

OTHER PUBLICATIONS

Murdoch, R., and K. M. Lagan. "The role of povidone and cadexomer iodine in the management of acute and chronic wounds." Physical Therapy Reviews 18.3 (2013): 207-216.*

(Continued)

*Primary Examiner* — Kim M Lewis
(74) *Attorney, Agent, or Firm* — Foley & Lardner LLP (57) ABSTRACT

A solid wound dressing material comprising: at least about 5 wt % collagen; from about 6 wt % to about 9 wt % polyvinylpyrrolidone triiodide (PVP-I); and from 0 wt % to about 20 wt % water; wherein the weight percentages are based on the dry weight of the composition. Also provided are methods of making such materials, and wound dressings comprising such materials. In another aspect the invention provides a solid wound dressing material comprising: at least about 5 wt % collagen; from about 10 wt % to about 90 wt % Cadexomer iodine; and from 0 wt % to about 20 wt % water, wherein the weight percentages are based on the dry weight of the composition. Also provided are wound dressings comprising the materials.

13 Claims, 5 Drawing Sheets

(51) Int. Cl.
*A61L 15/32* (2006.01)
*A61L 15/46* (2006.01)
*A61F 15/00* (2006.01)
*A61L 15/44* (2006.01)

(52) U.S. Cl.
CPC ......... *A61L 15/46* (2013.01); *A61L 2300/106* (2013.01); *A61L 2300/404* (2013.01)

(58) Field of Classification Search
CPC ...... A61K 6/0038; A61K 33/18; A61K 33/34; A61K 9/0014; A61K 8/20; A61K 9/08; A61K 2800/412; A61K 47/32; A61K 8/0279; A61K 8/25; A61K 8/19; A61K 9/06; A61L 15/225; A61L 15/325; A61L 15/28; A61L 15/44; A61L 15/425; A61L 26/0052; A61L 26/0095; A61L 2300/106; A61L 2300/404; A61L 15/24; A61L 15/40; A61L 15/46; C08L 89/06; C08L 5/08; A61F 15/002; A61F 2013/0071; A61F 2013/00659; A61F 2013/00676; A61F 2013/00719; A61F 2013/00723; A61F 2013/00089; A61F 13/00; A61F 13/00004; A61F 13/00008; A61F 13/00012; A61F 13/00017; A61F 13/00034
USPC ............ 602/41, 42, 43, 48, 49, 50; 424/404, 424/444–449; 514/17.2, 9.4; 523/122; 604/304–308
See application file for complete search history.

(56) References Cited

U.S. PATENT DOCUMENTS

| | | | | |
|---|---|---|---|---|
| 5,322,695 A * | 6/1994 | Shah | ..................... | A61K 9/7084 424/445 |
| 6,335,388 B1 * | 1/2002 | Fotinos | ................ | A61K 8/0208 424/443 |
| 6,399,092 B1 * | 6/2002 | Hobson | ............... | A61L 26/0052 424/443 |
| 7,871,699 B2 * | 1/2011 | Takaki | ..................... | A61L 15/46 428/355 BL |
| 8,124,826 B2 * | 2/2012 | Addison | ................. | A61L 15/28 602/48 |
| 2005/0191270 A1 * | 9/2005 | Gruening | ............. | A61K 9/0019 424/78.3 |
| 2006/0068013 A1 * | 3/2006 | DiTizio | ................ | A61K 9/7007 424/484 |
| 2007/0020318 A1 * | 1/2007 | Silcock | ................... | A61L 15/28 424/445 |
| 2007/0154530 A1 * | 7/2007 | Cullen | .................. | A61L 15/225 424/445 |
| 2011/0002971 A1 * | 1/2011 | Hassler | .................. | A01N 59/16 424/404 |

OTHER PUBLICATIONS

Sibbald RG, Leaper DJ, Queen D. (2011) "Iodine made easy" Wounds International; vol. 2:Issue2.*
European Search Report dated May 10, 2016, corresponding to European Application No. EP16154651.

* cited by examiner

WOUND DRESSINGS

The present invention relates to a novel wound dressing material, to wound dressings containing the material, and to methods of making such materials and wound dressings.

A wound dressing is an article used by a person for application to a wound to promote healing and/or prevent further harm. A dressing is designed to be in direct contact with the wound, which makes it different from a bandage, which is primarily used to hold a dressing in place.

Modern wound dressings include gauzes (which may be impregnated with an agent designed to help sterility or to speed healing), films, gels, foams, hydrocolloids, alginates, hydrogels and polysaccharide pastes, granules and beads. Many gauze dressings have a layer of non-stick film over the absorbent gauze to prevent the wound from adhering to the dressing.

Most of the advanced wound dressings are prepared from polymers which are natural or synthetic. One advantage of using natural polymers is their biocompatibility. Collagen is a natural material which has many applications in wound dressings. However, one of the drawbacks of using collagen as a wound dressing is that it has no antiseptic or antimicrobial properties.

The therapeutic properties of iodine were identified many years prior to its discovery. In the 4th century BC, Theophrastus, a pupil of Aristotle recorded that seaweeds and other iodine rich plants could be used to reduce the pain of sunburn. Davaine was the first to demonstrate the antimicrobial properties of iodine scientifically (1882) and reported that it was one of the most efficacious antiseptics.

Iodophors are complexes between iodine and a solubilising agent or carrier to increase the solubility and sustain the release of iodine. One of the first antiseptic iodine preparations to be used in wound care was Lugol's solution, a tincture developed in 1829 by J. G. A Lugol, a French Physician. Lugol's solution is an aqueous solution containing iodine (5%) and potassium iodide (10%); the presence of potassium iodide results in the formation of triiodide ions ($I^{3-}$) which enhances the solubility of elemental iodine. In other iodophor formulations, iodine is carried in aggregates or micelles which act as reservoirs of iodine. Once in contact with fluid, the micelles begin to slowly disperse resulting in the controlled release of low concentrations of iodine, preventing the generation of undesirable concentrations of free elemental iodine. Yet another iodophor is povidone iodine (PVP-I), which is a complex salt of polyvinyl pyrrolidinium with triiodide ions. Yet another iodophor is Cadexomer iodine, which is a hydrophilic modified starch polymer containing iodine within the helical matrix. Chemically it is a 2-hydroxy methylene cross-linked (1-4) [alpha]-D-glucan ether, containing iodine.

The activity of the iodophore is dependent on the amount of 'free' iodine (also known as available iodine) that potentially can be released from the iodophor. The available iodine content corresponds to the total iodine species that can be titrated against sodium thiosulfate. The available iodine content herein can be determined by the method in the Deutscher Arzneimittel Codex (DAC) 1986, 2nd Supplement 1990, for povidone-iodine.

Inadine® is a conventional PVP-I-containing wound dressing. Inadine consists of a knitted viscose fabric impregnated with a polyethylene glycol base containing 10% PVP-I, equivalent to 1.0% available iodine.

Iodoflex® is a layer of Iodosorb® ointment (cadexomer iodine beads incorporated into macrogol ointment base) sandwiched between two layers of gauze. The gauze acts as a protective carrier and also simplifies the application process; the first carrier layer is removed and the paste wafer is placed directly on the wound. The second gauze carrier is then removed and a secondary dressing applied. Iodosorb ointment has an iodine concentration of 0.9% w/w.

Oxozyme® is a hydrogel dressing which incorporates a biochemical system that increases the concentration of dissolved oxygen at the wound surface and liberates iodine from low levels (less than 0.04% w/w) of iodide ions present within the gel matrix.

Iodozyme is an occlusive, two component, hydrogel dressing which incorporates a biochemical system that generates hydrogen peroxide, which converts the low levels of iodide dispersed throughout the hydrogel into iodine.

JP 2001-17533 discloses a material for use in the treatment of skin ulcers, wherein the material comprises a collagen hydrogel containing PVP-I. The hydrogel suitably contains 0.05-5% w/v of PVP-I and 0.3-3% w/v of collagen, with the balance mainly water. The examples contain 0.33 wt. % collagen and 3.3 wt. % of PVP-I. The hydrogel materials are said to provide a combination of bactericidal properties with wound healing properties. However, these high-moisture hydrogel formulations would be difficult to sterilize and administer, and would require frequent dressing changes.

Iodine is often reported as having a negative impact on the cells involved in the wound healing process and controversy still surrounds its safety and efficacy due to issues with cytotoxicity, systemic absorption and delayed healing.

DE-A-10350654 discloses a collagen-containing substrate material which contains polymer particles containing an active substance for use as an implant or as a wound dressing. The substrate material is a freeze-dried collagen sponge. The active ingredient, which may comprise PVP-I, is microencapsulated in the polymer particles and released slowly in use.

EP-A-0 636 378 discloses absorbable composite materials comprising a collagen matrix reinforced with a layer of bioabsorbable polymer. The materials include a chemotherapeutic agent and are used in the treatment of periodontal disease.

EP-A-1795210 describes dressings that contain a combination of human recombinant collagen and oxidized regenerated cellulose in order to promote chronic wound healing. An unspecified amount of various medicaments, including povidone iodine, may be included in the dressings.

CN-A-101130105 describes a hydrogel wound dressing comprising 1-10 parts by weight PVP-I with 1-5 parts by weight collagen (as a selection from a list of possible irradiation stabilisers).

There remains a need for an improved wound dressing material which provides a good combination of wound healing properties and antimicrobial properties.

The present invention provides a solid wound dressing material comprising: at least about 5 wt % collagen; from about 6 wt % to about 9 wt % polyvinylpyrrolidone triiodide (PVP-I); and from 0 wt % to about 20 wt % water, wherein the weight percentages are based on the dry weight of the composition.

Suitably, the material comprises from about 7 wt. % to about 25 wt. % collagen, for example from about 8 wt. % to about 15 wt. % of collagen. Suitably, the material comprises from about 6.3 wt. % of PVP-I to about 8.5 wt. % of PVP-I, for example from about 7.5 wt. % PVP-I to about 8.5 wt. % PVP-I. Suitably, the composition comprises no more than about 10 wt. % of water, for example no more than about 5 wt. % of water.

Suitably, the solid wound dressing material of the invention comprises from about 7 wt % to about 25 wt. % collagen; from about 6 wt % to about 9 wt % polyvinylpyrrolidone triiodide (PVP-I); and from 0 wt % to about 10 wt % water, wherein the weight percentages are based on the dry weight of the composition.

More suitably, the solid wound dressing material of the invention comprises from about 5 wt % to about 15 wt. % collagen; from about 6.3 wt % to about 8.5 wt % polyvinylpyrrolidone triiodide (PVP-I); and from 0 wt % to about 10 wt % water, wherein the weight percentages are based on the dry weight of the composition.

Suitably, the solid wound dressing material of the invention comprises PVP-I and collagen in a weight ratio of 0.3:1 to 1.5:1 PVP-I:collagen, more suitably 0.4:1 to 1.2:1, most suitably 0.8:1 to 1.1:1.

The PVP-I suitably has an available iodine content of from about 5% to about 15%, more suitably from about 9% to about 12%, before incorporation into the material of the invention. It follows that the materials of the invention suitably have an available iodine content as defined above of from about 0.5% to about 1.5%, for example about 0.7% to about 1.2%, calculated as weigh percent on a dry weight basis.

Suitably, the PVP-I is uniformly dissolved or dispersed in or on a solid matrix containing the collagen. That is to say, the PVP-I is not present in the materials as a second phase such as in microcapsules or microparticles containing the PVP-I, but is uniformly dispersed throughout the material. Suitably, the material is a product obtainable by drying a solution of the PVP-I in a solvent also containing dissolved or dispersed collagen, or it is a product obtainable by coating a solid matrix containing collagen with a solution of PVP-I in a suitable solvent, followed by removal of the solvent. Such materials have the PVP-I intimately mixed with the collagen at the molecular level, thereby achieving maximum synergistic effect of the collagen and PVP-I as explained further below.

In a second aspect, the present invention provides a solid wound dressing material comprising: at least about 5 wt % collagen; from about 10 wt % to about 90 wt % Cadexomer iodine; and from 0 wt % to about 20 wt % water, wherein the weight percentages are based on the dry weight of the composition.

Suitably, the material comprises from about 7 wt. % to about 25 wt. % collagen, for example from about 8 wt. % to about 15 wt. % of collagen. Suitably, the material comprises from about 20 wt. % of Cadexomer iodine to about 70 wt. % of Cadexomer iodine, for example from about 25 wt. % Cadexomer iodine to about 65 wt. % Cadexomer iodine. Suitably, the composition comprises no more than about 10 wt. % of water, for example no more than about 5 wt. % of water.

The Cadexomer iodine suitably has an available iodine content of from about 0.5% to about 1.5%, more suitably from about 0.8% to about 1.2%, before incorporation into the material of the invention. It follows that the materials according to this aspect of the invention suitably have an available iodine content as defined above of from about 0.1% to about 1.4%, for example about 0.5% to about 1%, calculated as weigh percent on a dry weight basis. The term "Cadexomer iodine" herein encompasses any complex of iodine with a polysaccharide, in particular complexes of iodine with dextrin or cross-linked dextrin. The Cadexomer iodine may be prepared, for example, as described in U.S. Pat. No. 4,010,259 or WO-A-2008117300.

The balance of the compositions according to any aspect of the present invention may comprise plasticisers, non-aqueous solvents, therapeutic agents and/or polymers other than collagen. The other polymers may, for example comprise biopolymers or bioabsorbable polymers of natural or synthetic origin.

Any type of collagen may be used in the wound dressing compositions of the present invention, e.g. collagen of bovine, ovine, porcine, equine, recombinant, or human origin. Bovine collagen, for example extracted from bovine corium, is suitable. Atelocollagen may also be used.

The wound dressing material suitably comprises from about 5 wt. % to about 85 wt. % of one or more plasticisers, based on the dry weight of the material. The amount of plasticiser is suitably from about 53 wt % to about 88 wt %, for example from about 60 wt % to 85 wt % or from or from about 65 wt % to about 84 wt % or from about 75 wt % to about 83 wt % of the material. Suitable plasticisers in include dihydric and polyhydric alcohols having from 2 to 20 carbon atoms, such as diethylene glycol, triethylene glycol, glycerol. Further plasticisers include polyethylene glycols, which also act as surfactants, for example having molecular weights in the range 200 to 20000, for example peg 200 and peg 4000.

The materials may further comprise other medically acceptable polymeric matrix materials, including water soluble matrix polymers such as PVP and polyvinyl alcohols, and polymers that degrade in vivo such as polylactide/polyglycolide copolymers and poly—epsilon-caprolactone. Further polymers that could be incorporated into the material include any of the medically acceptable biopolymers such as alginates, carboxymethylcellulose, hydroxyethylcellulose, oxidized regenerated cellulose. The amount of polymers other than collagen in the materials is suitably up to about 75 wt. %, for example from about 1 wt. % to about 50 wt. % based on the dry weight of the material.

The wound dressing compositions of the present invention may optionally further comprise other therapeutic agents selected from the group consisting of vitamins; further antiseptics; anti-inflammatory agents; enzyme inhibitors; immunostimulants; immunosuppressive agents; local anaesthetics; anti-infectives (e.g. anti-bacterial agents), antiviral agents; antioxidants; steroid hormones and minerals. Suitably, these further therapeutic agents are present in an amount of from about 0.001 wt % to about 10 wt %, for example from about 0.01 wt % to about 5 wt %, typically from about 0.1 wt % to about 2 wt %.

The materials of the invention provide an excellent combination of wound healing properties with antimicrobial properties. This is demonstrated in the examples below, in which comparisons are shown between the amounts of PVP-I and collagen used in the present invention and dressings having different amounts of PVP-I, and the iodine dressings conventionally used in the prior art. It is to be expected that the same effect will be seen for other iodophors, such as cadexomer iodine.

Without wishing to be bound by any theory, it seems that the collagen mitigates the cytotoxic properties of the PVP-I. The use of at least about 5 wt. % collagen in the dressing, together with an amount of PVP-I in the narrow range of 6 to 9 wt. %, allows a combination of good antimicrobial properties with low cytotoxicity and good wound healing properties.

A further advantage is that the addition of PVP-I to a solid collagen dressing provides a wound dressing that is easy to apply, particularly in contrast to the conventional 10%

PVP-I solution which, being a liquid, is difficult to apply to wounds in a localised manner.

A further advantage is that the compositions of the present invention display unexpectedly superior antimicrobial activity in zone of inhibition assay when compared to Inadine. This is also demonstrated in the examples.

The materials of the invention are solids, for example films, coatings, sponges or nonwoven or woven fabrics. Most suitably, the materials of the invention are in the form of a plasticised film. Suitably, the wound dressing material according to the present invention is in the form of a flexible film, which may be continuous or interrupted (e.g. perforated).

In certain embodiments, the wound dressing material according to the present invention may be in the form of a freeze-dried or solvent-dried bioabsorbable sponge for application to a chronic wound. Suitably, the average pore size of the sponge is in the region of 10-500 μm, more preferably about 100-300 μm.

Suitably, the wound dressing material is in the form of a sheet, for example a sheet of substantially uniform thickness. The area of the sheet is typically from about 1 cm$^2$ to about 400 cm$^2$, and the thickness typically from about 1 mm to about 10 mm.

The present invention further provides a wound dressing comprising the wound dressing material according to the present invention.

The wound dressing is suitably in sheet form and comprises a sheet (layer) of the material according to the invention. However, alternative shapes such as cavity filling wounds are also envisaged. The layer according to the invention would normally be the wound contacting layer in use, but in some embodiments it could be separated from the wound by a liquid-permeable top sheet. Suitably, the area of the sheet of material according to the invention is from about 1 cm$^2$ to about 400 cm$^2$, more suitably from about 4 cm$^2$ to about 100 cm$^2$.

Suitably, the wound dressing further comprises a backing sheet extending over the active layer according to the invention, opposite to the wound facing side of the said active layer. Suitably, the backing sheet is larger than the layer according to the invention such that a marginal region of width 1 mm to 50 mm, suitably 5 mm to 20 mm extends around the said layer to form a so-called island dressing. In such cases, the backing sheet is suitably coated with a pressure sensitive medical grade adhesive in at least its marginal region.

Suitably, the backing sheet is substantially liquid-impermeable. The backing sheet is suitably semipermeable. That is to say, the backing sheet is suitably permeable to water vapour, but not permeable to liquid water or wound exudate. Suitably, the backing sheet is also microorganism-impermeable. Suitable continuous conformable backing sheets will suitably have a moisture vapor transmission rate (MVTR) of the backing sheet alone of 300 to 5000 g/m$^2$/24 hrs, suitably 500 to 2000 g/m$^2$/24 hrs at 37.5° C. at 100% to 10% relative humidity difference. The backing sheet thickness is suitably in the range of 10 to 1000 micrometers, more suitably 100 to 500 micrometers. It has been found that such moisture vapor transmission rates allow the wound under the dressing to heal under moist conditions without causing the skin surrounding the wound to macerate.

Suitable polymers for forming the backing sheet include polyurethanes and poly alkoxyalkyl acrylates and methacrylates such as those disclosed in GB-A-1280631. Suitably, the backing sheet comprises a continuous layer of a high density blocked polyurethane foam that is predominantly closed-cell. A suitable backing sheet material is the polyurethane film available under the Registered Trade Mark ESTANE 5714F.

The adhesive (where present) layer should be moisture vapor transmitting and/or patterned to allow passage of water vapor therethrough. The adhesive layer is suitably a continuous moisture vapor transmitting, pressure-sensitive adhesive layer of the type conventionally used for island-type wound dressings. The basis weight of the adhesive layer is suitably 20 to 250 g/m$^2$, and more suitably 50 to 150 g/m$^2$. Polyurethane- or polyacrylate-based pressure sensitive adhesives are preferred.

Further layers of a multilayer absorbent article may be built up between the layer according to the present invention and the protective sheet. For example, these layers may comprise one or more absorbent layers between the layer according to the invention and the protective sheet, especially if the dressing is for use on exuding wounds. The optional absorbent layer may be any of the layers conventionally used for absorbing wound fluids, serum or blood in the wound healing art, including gauzes, nonwoven fabrics, superabsorbents, hydrogels and mixtures thereof. Suitably, the absorbent layer comprises a layer of absorbent foam, such as an open celled hydrophilic polyurethane foam prepared in accordance with EP-A-0541391. In other embodiments, the absorbent layer may be a nonwoven fibrous web, for example a carded web of viscose staple fibers. The basis weight of the absorbent layer may be in the range of 50-500 g/m$^2$, such as 100-400 g/m$^2$.

The wound facing surface of the dressing is suitably protected by a removable cover sheet. The cover sheet is normally formed from flexible thermoplastic material. Suitable materials include polyesters and polyolefins. Suitably, the adhesive-facing surface of the cover sheet is a release surface. That is to say, a surface that is only weakly adherent to the wound facing layers and the adhesive on the backing sheet to assist peeling of the adhesive layer from the cover sheet. For example, the cover sheet may be formed from a non-adherent plastic such as a fluoropolymer, or it may be provided with a release coating such as a silicone or fluoropolymer release coating.

Typically, the wound dressing according to the present invention is sterile and packaged in a microorganism-impermeable container. It is an advantage of the materials according to the present invention that their low water content makes them stable to sterilization by gamma-radiation or autoclaving.

In a further aspect, the present invention provides method of treatment of a wound comprising applying thereto an effective amount of a dressing material according to the present invention. Suitably, the treatment comprises applying to said wound a dressing according to the present invention.

The material is suitably applied to the wound for a period of at least about 1 hour, more suitably from about 4 hours to about 4 weeks, for example from about 1 day to about 14 days, optionally with dressing changes during the course of the treatment.

As used herein, the term "wound" means a break in the skin. Examples of wounds for which the present invention is particularly suited include skin ulcers (e.g. bed sores, diabetic ulcers and leg ulcers), burns, surgical wounds, abrasions and acute wounds. The material may be applied to wounds already showing clinical signs of infection.

The present invention further provides a method of making a wound dressing material according to the present invention, said method comprising: (a) forming a slurry comprising: a solvent, collagen dispersed in said solvent; and PVP-I dispersed in said solvent; followed by (b) removing the solvent from the slurry.

The present invention is now described, by way of illustration only, with reference to the accompanying drawings, in which.

The invention is further illustrated by the following examples. It will be appreciated that the examples are for illustrative purposes only and are not intended to limit the invention as described above. Modification of detail may be made without departing from the scope of the invention as defined in the accompanying claims.

EXAMPLES

Wound dressing films were produced according to the following method. The quantities of ingredients in Table 1 were blended until uniform in the following order of addition: collagen slurry, acetic acid, PVP-I paste and glycerol.

TABLE 1

| Slurry ID# | Collagen slurry/g | Acetic acid (0.05M)/ml | PVP-I paste/g | Glycerol/ml |
|---|---|---|---|---|
| 1 | 99.5 | 96.5 | 0 | 4 |
| 2 | 99.5 | 94.3 | 2.2125 | 4 |
| 3 | 99.5 | 92.0 | 4.5 | 4 |
| 4 | 99.5 | 87.6 | 8.9 | 4 |
| 5 | 99.5 | 78.7 | 17.8 | 4 |
| 6 | 99.5 | 60.9 | 35.6 | 4 |
| 7 | 91.3 | 39.6 | 65.4 | 3.7 |
| 8 | 99.5 | 7.5 | 89.0 | 4 |

The collagen slurry contained bovine collagen (2.01% solids in aqueous acetic acid pH 2.9-3.1). Care was taken not to over-manipulate the collagen.

The PVP-I paste contained 48.63% Lutrol 400 (a polyethylene glycol having an average molecular weight of 400 and a general formula HO—[—$CH_2$—$CH_2$—O—]$_n$—H, wherein n=8); 35.73% PEG 4000; 10.68% PVP-I and 4.96% water.

The slurries produced were degassed in a vacuum chamber and poured into 100 $cm^2$ dishes as indicated in Table 2. The percentage PVP-I and collagen in the wet compositions was calculated and is also shown in Table 2.

TABLE 2

| Film ID | Slurry ID# (see table 1) | Slurry added to 100 $cm^2$ dish/g | Col per 100 $cm^2$ dish/g | PVP-I per 100 $cm^2$ dish/g | wt % PVP-I in wet composition | wt % col in wet composition |
|---|---|---|---|---|---|---|
| CC1* | 1 | 62 | 0.617 | 0.00 | 0% | 0.99% |
| CC2* | 2 | 93 | 0.925 | 0.00 | 0% | 0.99% |
| A* | 2 | 62 | 0.617 | 0.073 | 0.12% | 0.99% |
| B* | 2 | 93 | 0.925 | 0.109 | 0.12% | 0.99% |
| C* | 3 | 93 | 0.925 | 0.222 | 0.24% | 0.99% |
| D | 4 | 93 | 0.925 | 0.440 | 0.47% | 0.99% |
| E | 5 | 62 | 0.617 | 0.586 | 0.95% | 0.99% |
| F* | 6 | 93 | 0.925 | 1.759 | 1.89% | 0.99% |
| G* | 7 | 93 | 0.849 | 3.232 | 3.48% | 0.91% |
| H* | 8 | 62 | 0.617 | 2.931 | 4.73% | 0.99% | col = collagen;
CC = Collagen control;
*= reference example

The films were dried overnight in air until dry to the touch. Based on weight loss on drying it was deduced that more than 90% of the water and acetic acid originally present in the slurry were removed on drying. The calculated percentage compositions of the dry films are shown in Table 3. Percentages are calculated on a dry weight basis, i.e. based on all the components of the starting slurry except for water and acetic acid.

TABLE 3

| Film ID | wt % PVP-I in composition | wt % Collagen in composition | wt % water in composition | Ratio of PVP-I:collagen |
|---|---|---|---|---|
| CC1* | 0 | 28 | <5% | 0 |
| CC2* | 0 | 28 | <5% | 0 |
| A* | 2.6 | 22 | <5% | 0.12:1 |
| B* | 2.6 | 22 | <5% | 0.12:1 |
| C* | 4.3 | 18 | <5% | 0.24:1 |
| D | 6.3 | 13 | <5% | 0.48:1 |
| E | 8.3 | 8.7 | <5% | 0.95:1 |
| F* | 9.7 | 5.1 | <5% | 1.9:1 |
| G* | 10.7 | 2.8 | <5% | 3.8:1 |
| H* | 10.9 | 2.3 | <5% | 4.8:1 |

CC = Collagen control;
*= reference example

Prior to any in vitro tests, the films were sterilised at 18.5 KGy.

Procedure 1

The films prepared according to the above examples and reference examples were subjected to a zone-of-inhibition test to determine their antimicrobial activity against *Pseudomona aeruginosa*. For comparison purposes, inadine, iodoflex, oxozyme and iodozyme (four conventional iodine-producing wound dressings) were also tested. A small square of film 6.25 $cm^2$ was placed centrally in a petri dish inoculated with 10 *Pseudomonas aeruginosa* from a stock of approx $1.0\times10^7$ CFU/ml and the zone of inhibition of the *Pseudomonas aeruginosa* from the edge of the film was measured in mm after overnight incubation at 37° C.

Figure 1:
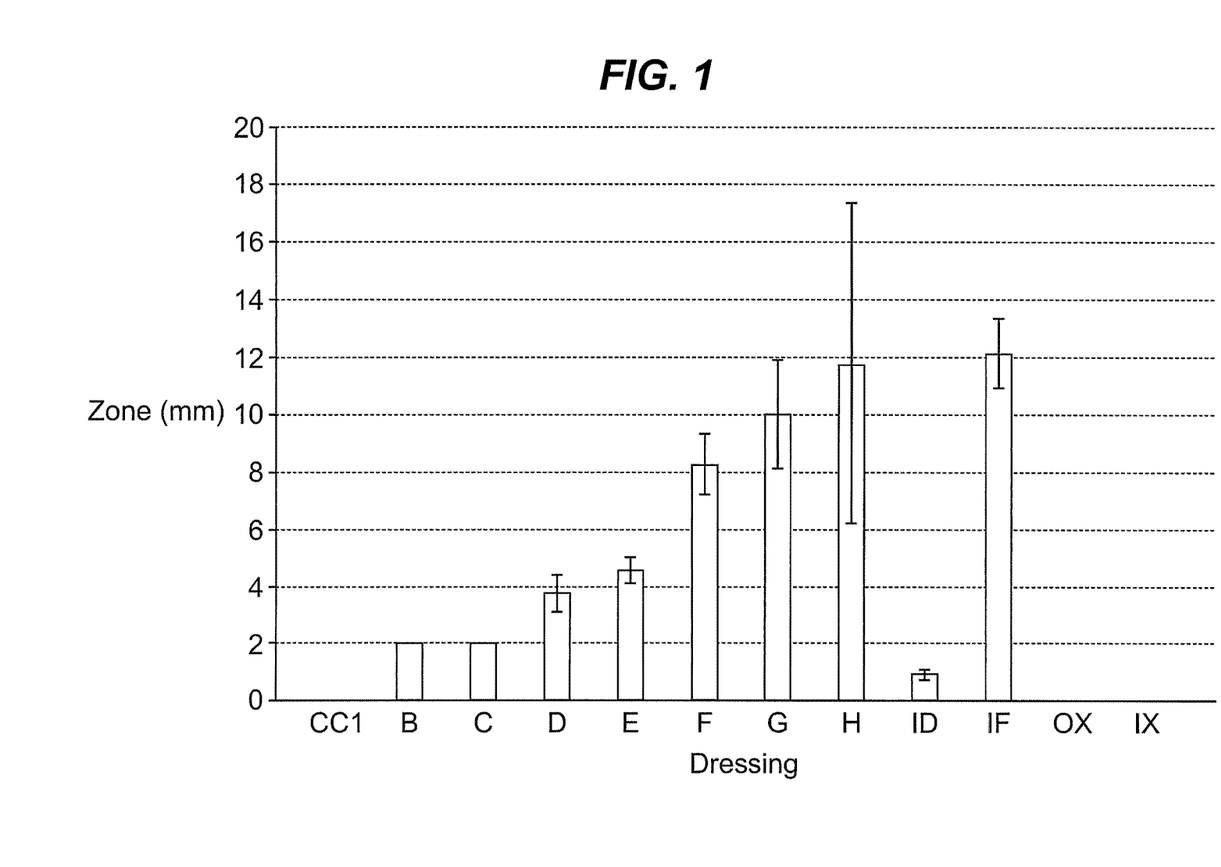
FIG. 1 shows the zone of inhibition formed by materials according to the invention and comparative materials when tested against *Pseudomona aeruginosa*.

FIG. 1 shows a bar chart with the zone of inhibition measurements for the films of the examples and reference examples above, and for each of inadine (ID), iodoflex (IF), oxozyme (OX) and iodozyme (IX).

The data in FIG. 1 show that zones of inhibition in the range 0-2 mm were provided by the collagen control, films B and C, and the inadine, oxozyme and iodozyme dressings. Inhibition zones greater than 2 mm were provided by films D-H, and iodoflex.

These data show that the greater the amount of PVP-I in the film, the greater the inhibition zone of *Pseudomonas aeruginosa*. Significant inhibition, i.e. >2 mm, begins at PVP-I concentrations of around 6 wt %.

Procedure 2

The films prepared according to the examples and reference examples above were tested to determine their antimicrobial activity against *Staphylococcus aureus*. For comparison purposes, inadine (ID), iodoflex (IF), oxozyme (OX) and iodozyme (IX) were also tested. A small square of film 6.25 cm$^2$ was placed centrally in a petri dish inoculated with approx 1.5×10$^5$ CFU/ml *Staphylococcus aureus* and the zone of inhibition of the *Staphylococcus aureus* from the edge of the film was measured in mm after overnight incubation at 37° C.

Figure 2:
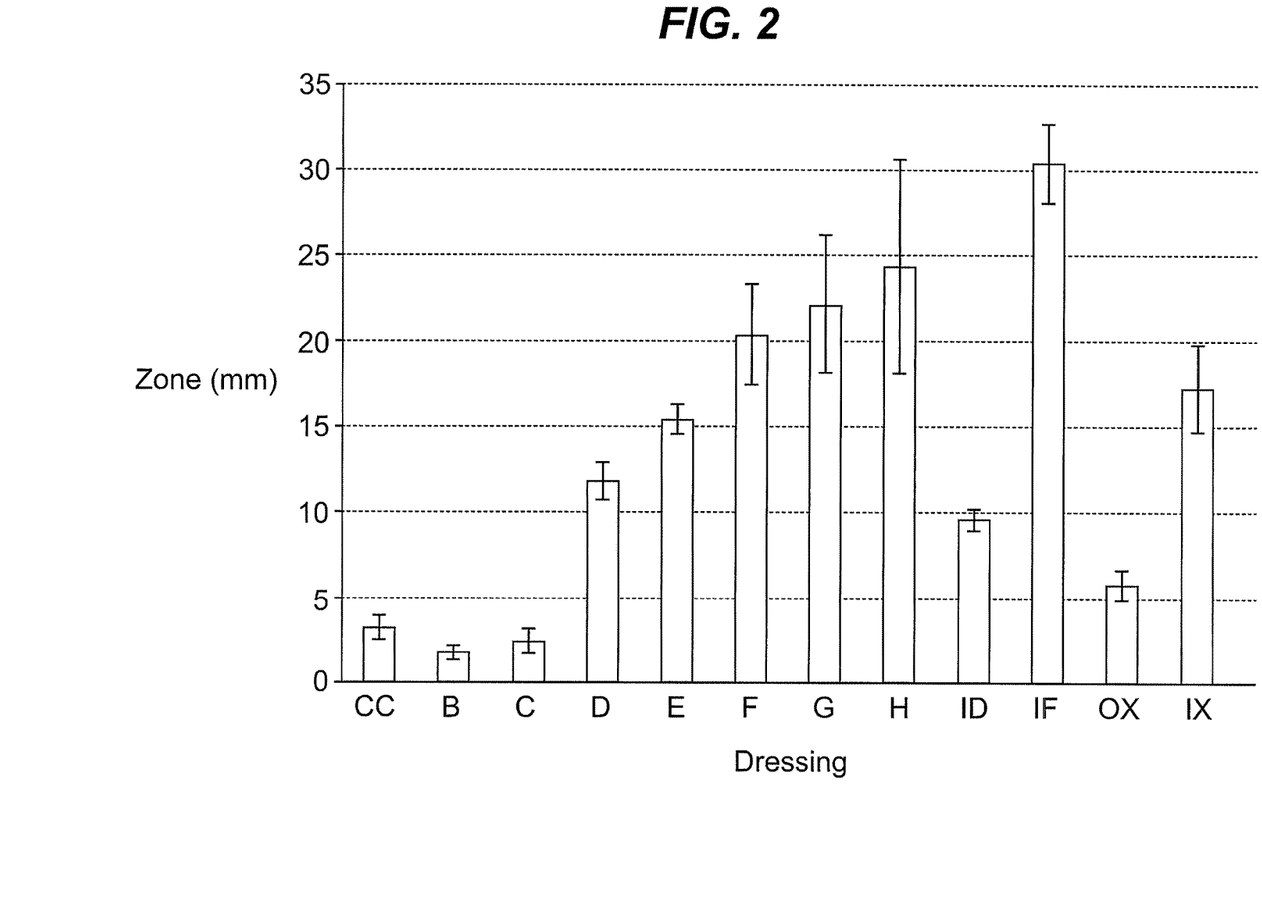
FIG. 2 shows the zone of inhibition formed by materials according to the invention and comparative materials when tested against *Staphylococcus aureus*.

FIG. 2 shows a bar chart with the zone of inhibition measurements for the films of the examples and reference examples above, and for each of inadine, iodoflex, oxozyme and iodozyme.

The data in FIG. 2 show that 0-4 mm zones of inhibition were provided by the collagen control and films B-C (film A was not tested). Inhibition zones greater than 10 mm were provided by films D-H and iodoflex and iodozyme.

These data show that the greater the amount of PVP-I in the film, the greater the inhibition zone of *Staphylococcus aureus*. Significant inhibition, i.e. >10 mm, begins at PVP-I concentrations of around 6 wt %.

Procedure 3

The cytotoxicity of the film compositions of the examples and reference examples above towards human keratinocytes was evaluated as follows.

Figure 3:
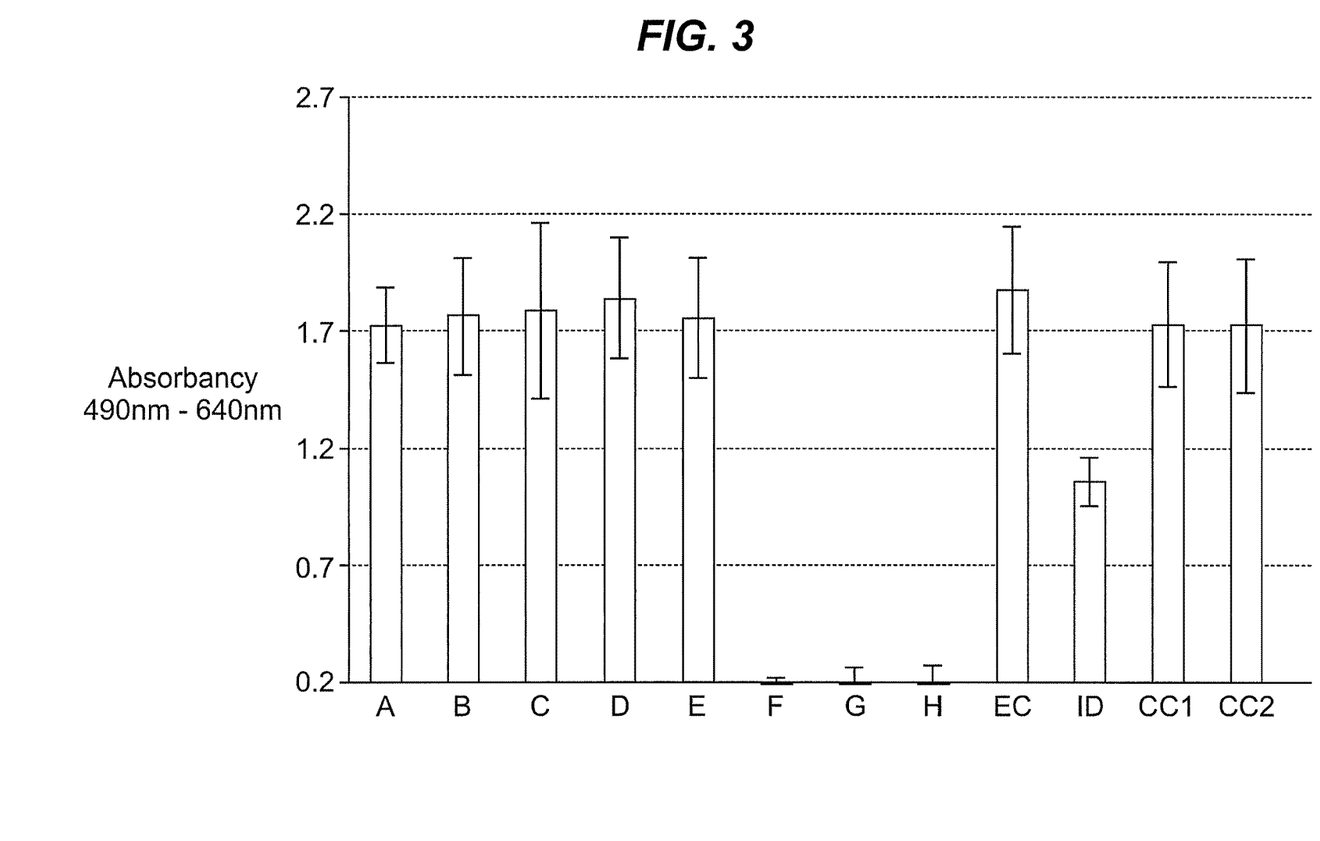
FIG. 3 shows the MKEK cell metabolic activity of primary adult human keratinocytes measured 24 hours after incubation with wound dressing materials according to the invention and comparative materials.

The cell metabolic activity of primary adult human keratinocytes was measured after 24 hours incubation with the films of the examples and reference example. The cell metabolic activity is measured using a standard MTS-PES cell proliferation assay. Reagent was added to the cells in the culture 1 part reagent and 5 parts media and colour change is measured after 3 hours incubation at 37° C. 5% CO$_2$ in humidified atmosphere. The assay was carried out 24 hours after challenge with the prototype films. FIG. 3 shows measured absorbance of the medium at 490-640 nm, where high absorbance signifies high cell metabolic activity (i.e. low cytotoxicity). It can be seen that for the films A-E the metabolic activity is unchanged from the collagen controls (CC) and the empty control (EC). However, the metabolic activity is very low for Films F-H These data show no significant inhibition of metabolic activity for the films containing less than about 9 wt. % PVP-I. Interestingly, the performance of films A-E in this test is even better than the performance of the Inadine (ID) reference example.

Procedure 4

The effects of the films compositions of the examples and reference examples on cell proliferation and wound healing was evaluated using an in vitro scratch wound response test. Keratinocytes were grown to confluence and a thin "wound" introduced by scratching with a pipette tip. Cells at the wound edge polarise and migrate into the wound space. The percent wound closure was measured at 1, 2, 4 and 6 hours from initiation using standard protocols. The effect of the various film materials of the examples and reference examples was determined by placing samples of these materials on top of the scratch "wound".

Figure 4:
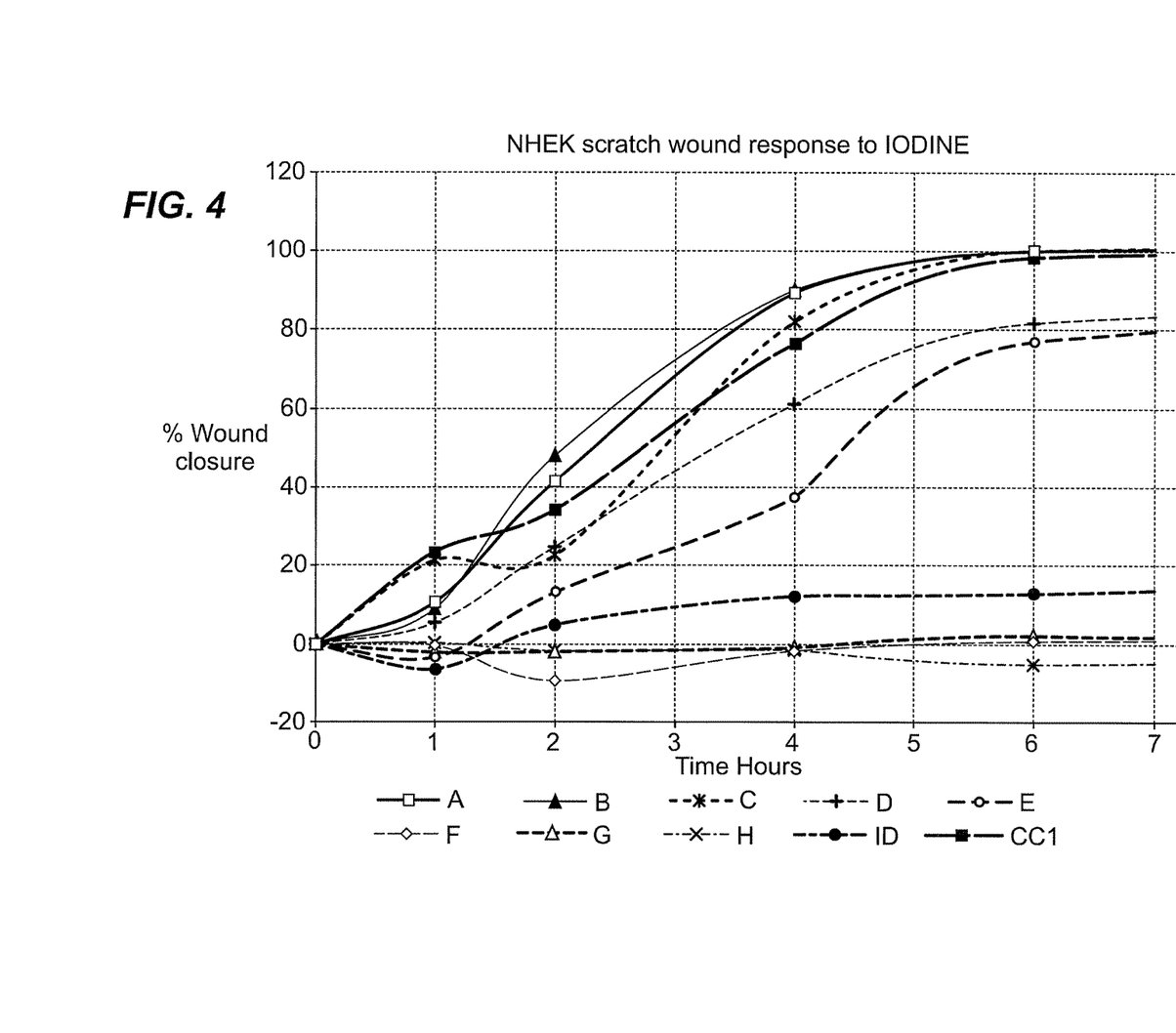
FIG. 4 shows the human keratinocyte scratch response test performance versus time for materials according to the invention and comparative materials.

The results are shown in FIG. 4. It can be seen that the films containing higher levels of PVP-I clearly inhibit wound healing in the scratch test. However, the films A to E do not significantly inhibit wound healing relative to the collagen control. It can further be seen that the Inadine (ID) reference example also significantly inhibits the scratch response wound healing.

It can thus be seen that Films D and E provide the combination of good antimicrobial properties and good wound healing properties, which can be attributed to the amounts of PVP-I present in the films in combination with the collagen.

It can also be seen from the above comparisons that the films D and E of the present invention are superior to Inadine®, which is the current best commercial iodine dressing.

This superiority is shown in the combination of antimicrobial properties, the lower cytotoxicity, and better wound healing as determined by the scratch test.

Figure 5:
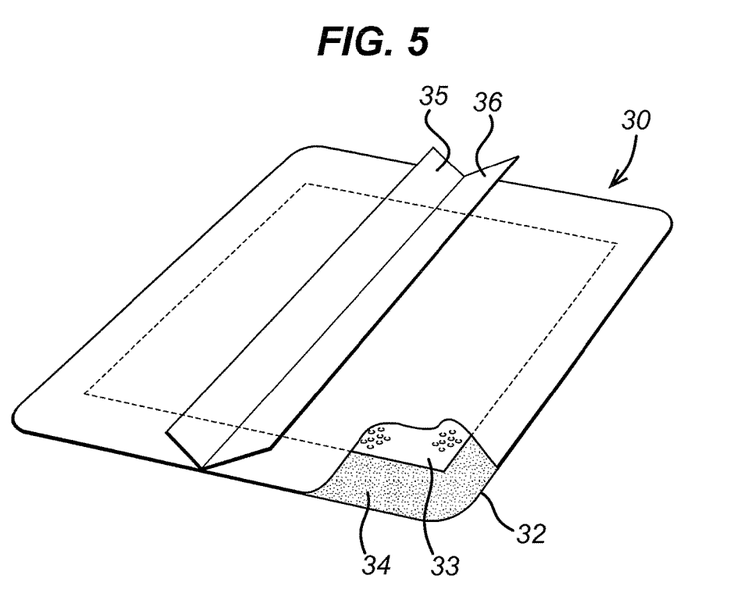
FIG. 5 shows a bottom perspective view of a wound dressing according to the invention.

Referring to FIG. 5, the wound dressing 30 according to the present invention is an island-type, self-adhesive wound dressing comprising a backing layer 32 of microporous liquid-impermeable polyurethane foam. The backing layer 32 is permeable to water vapor, but impermeable to wound exudate and microorganisms.

The backing layer 32 is coated with a substantially continuous layer of pressure-sensitive polyurethane adhesive. A rectangular island 33 of a wound dressing material according to the invention in sheet form, made in accordance with Example E above, is adhered to a central region of the backing layer 32, which may be adhesive-coated, such that an adhesive-coated margin 34 of the backing layer 32 sheet extends around the island for attachment of the dressing to the skin around a wound. The dressing further comprises protective, release-coated cover sheets 35, 36. These cover sheets are removed immediately before use of the dressing.

Figure 6:
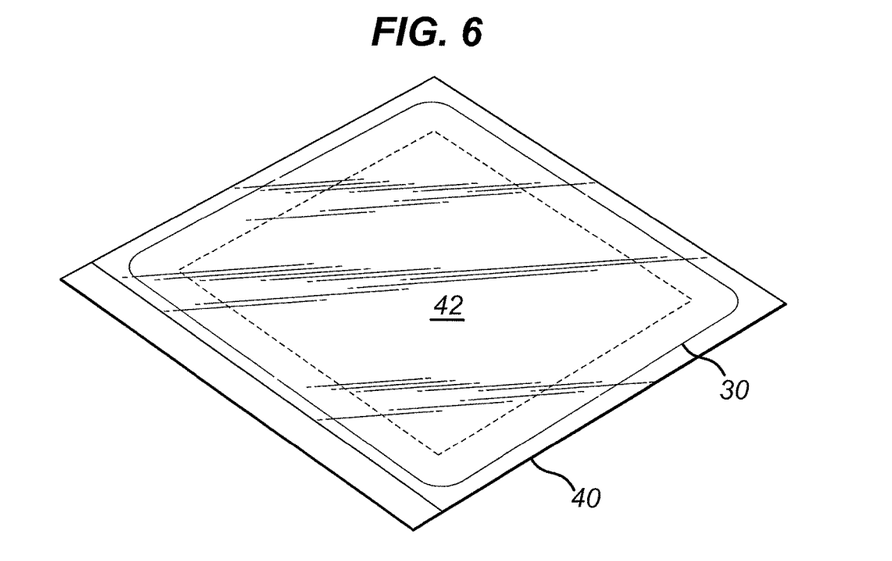
FIG. 6 shows a bottom perspective view of the wound dressing of FIG. 5 in a package.

Referring to FIG. 6, the wound dressing 30 is sterile and packaged in a microorganism-impermeable pouch 40 having a transparent front panel 42 prior to use.

The above embodiments have been described by way of example only. Many other examples falling within the scope of the accompanying claims will be apparent to the skilled reader.

The invention claimed is:

1. A solid wound dressing material comprising:
   at least 5 wt % collagen;
   from 6 wt % to 9 wt % polyvinylpyrrolidone triiodide (PVP-I); and
   from 0 wt % to 20 wt % water;
   wherein the PVP-I and collagen are present in a weight ratio of 0.48:1 to 0.95:1 PVP-I:collagen, and
   wherein the weight percentages are based on dry weight.

2. A solid wound dressing material according to claim 1, comprising:
   from 7 wt % to 15 wt. % collagen;
   from 6 wt % to 9 wt % polyvinylpyrrolidone triiodide (PVP-I); and
   from 0 wt % to 10 wt % water;
   wherein the weight percentages are based on dry weight.

3. A solid wound dressing material according to claim 1, comprising:
   from 5 wt % to 15 wt. % collagen;
   from 6.3 wt % to 8.5 wt % polyvinylpyrrolidone triiodide (PVP-I); and
   from 0 wt % to 10 wt % water;
   wherein the weight percentages are based on dry weight.

4. The wound dressing material of claim 1, further comprising from 5 wt. % to 85 wt. % of one or more plasticisers, based on dry weight.

5. The wound dressing material according to claim 1, wherein the material is in the form of a plasticized film.

6. The wound dressing material of claim 1, wherein the PVP-I and collagen are present in a weight ratio of 0.8:1 to 0.95:1 PVP-I:collagen.

7. The wound dressing material of claim 1, further comprising at least 53 wt. % of one or more plasticisers, based on dry weight.

8. A wound dressing comprising:
   a solid wound dressing material, comprising:
   at least 5 wt % collagen,
   from 6 wt % to 9 wt % polyvinylpyrrolidone triiodide (PVP-I), and
   from 0 wt % to 20 wt % water,
   wherein the PVP-I and collagen are present in a weight ratio of 0.48:1 to 0.95:1 PVP-I:collagen, and
   wherein the weight percentages are based on dry weight; and
   a backing layer.

9. A wound dressing according to claim 8, wherein the wound dressing is sterile and packaged in a microorganism-impermeable container.

10. The wound dressing of claim 8, wherein the solid wound dressing material further comprises at least 53 wt. % of one or more plasticisers, based on dry weight.

11. A method of making a wound dressing material having PVP-I and collagen present in a weight ratio of 0.48:1 to 0.95:1 PVP-I:collagen, said method comprising:
   (a) forming a slurry comprising:
      a solvent;
      collagen dispersed in said solvent; and
      PVP-I dispersed in said solvent; followed by
   (b) removing the solvent from the slurry.

12. A method according to claim 11, wherein said solvent is an aqueous solvent having pH less than 6.

13. The method of claim 11, wherein the solid wound dressing material further comprises at least 53 wt. % of one or more plasticisers, based on dry weight.

* * * * *